United States Patent
Roederer et al.

(10) Patent No.: US 6,178,382 B1
(45) Date of Patent: Jan. 23, 2001

(54) METHODS FOR ANALYSIS OF LARGE SETS OF MULTIPARAMETER DATA

(75) Inventors: Mario Roederer, Redwood City; Adam S. Treister, San Carlos; Martin Bigos, San Francisco; David R. Parks, San Francisco; Wayne A. Moore, San Francisco; Leonore A. Herzenberg, Stanford, all of CA (US)

(73) Assignee: The Board of Trustees of the Leland Stanford Junior University, Stanford, CA (US)

( * ) Notice: Under 35 U.S.C. 154(b), the term of this patent shall be extended for 0 days.

(21) Appl. No.: 09/103,284

(22) Filed: Jun. 23, 1998

(51) Int. Cl.[7] .............................. G01N 33/50; G06F 19/00
(52) U.S. Cl. .............................. 702/21; 702/19; 345/356; 435/7.1; 435/7.2; 435/69.3
(58) Field of Search .................... 702/19–21; 345/346, 345/356; 435/7.1, 7.2, 69.3

(56) References Cited

U.S. PATENT DOCUMENTS

| | | | |
|---|---|---|---|
| 4,284,412 | * 8/1981 | Hansen et al. | 435/7.24 |
| 4,661,913 | * 4/1987 | Wu et al. | 702/19 |
| 4,845,653 | * 7/1989 | Conrad et al. | 345/346 |
| 5,605,805 | * 2/1997 | Verwer et al. | 435/7.24 |
| 5,862,304 | * 1/1999 | Raudin et al. | 706/25 |
| 5,968,755 | * 10/1999 | Roederer et al. | 435/69.3 |

* cited by examiner

Primary Examiner—Marc S. Hoff
Assistant Examiner—Bryan Bui
(74) Attorney, Agent, or Firm—Lumen Intellectual Property Services

(57) ABSTRACT

This invention relates a series of methods for the visual representation and subsequent application of analyses on complex data sets. In particular, this invention is useful for the analysis of multiple sample sets that share common features, for which similar types of analyses are desired. Three concepts are embodied to aid in this analysis: "Functional equivalence by Algorithmic Polymorphism" (FEAP), in which an analysis algorithm is abstracted through the use of an associated name; a genealogical metaphor for the representation of successive or parallel analysis steps, in which "families" of analyses can be easily copied between different sample data sets; and batch analysis through the creation of multi-sample analysis surrogates (MSAS), which are groups of samples wherein analyses applied to an MSAS is then applied to every sample within the MSAS group. This invention has particular utility in the analysis of data derived from flow cytometers, the analysis of complex demographic data, and other similar data sets.

18 Claims, 15 Drawing Sheets

| Sort... | Name | Statistic | *Cells |
|---|---|---|---|
| ▽ | A01:PBMC | | 50000 |
| ▽ | Lymphs | 77.99% | 38997 |
| ▽ | B cells | 2.00% | 1001 |
| | B1 B | 1.37% | 687 |
| | Conventional B | 0.60% | 299 |
| ▽ | NK | 9.38% | 4690 |
| | CD56- | 2.18% | 1091 |
| | CD56+CD57+ | 1.94% | 972 |
| | CD56+CD57- | 4.67% | 2335 |
| | T cells | 65.13% | 32563 |
| ▽ | CD 4 T | 44.25% | 22127 |
| ▽ | M1 | 5.19% | 2593 |
| | CDw60+ | 2.72% | 1362 |
| | CDw60- | 2.33% | 1167 |
| ▽ | M2 | 10.58% | 5292 |
| | CDw60+ | 4.03% | 2017 |
| | CDw60- | 6.31% | 3156 |
| ▽ | M3 | 2.71% | 1356 |
| | CDw60+ | 1.00% | 501 |
| | CDw60- | 1.66% | 830 |
| | Naive | 23.98% | 11990 |
| ▽ | CD5-T | 0.15% | 74 |
| | CDw60+ | 0.04% | 20 |
| | CDw60- | 0.11% | 54 |
| ▽ | CD8 T | 19.46% | 9731 |
| ▽ | M1 | 1.33% | 666 |
| | CDw60+ | 0.26% | 132 |
| | CDw60- | 1.06% | 529 |
| | M2 | 2.86% | 1431 |
| | CDw60+ | 0.69% | 347 |
| | CDw60- | 2.10% | 1051 |
| ▽ | M3 | 3.20% | 1598 |
| | CDw60+ | 0.20% | 98 |
| | CDw60- | 2.99% | 1496 |
| | Naive | 11.28% | 5641 |

FIG. 5

Analysis Node Information
  Name
  Reference to Parent Node
  Reference to Child Node
  Reference to Sibling Node
  Reference to Algorithm
  Data type required by Algorithm (Input)
  Data type generated by Algorithm (Output)

FIG. 6A

Special analysis nodes:
  Data set node:
    Parent node = nil
    Algorithm is a function to read the data from a file
    Data type required by Algorithm is unspecified MSAS node:
    Parent node = nil
    Algorithm is unspecified
    Data type required by Algorithm is unspecified
    Also contains list of member data set nodes

FIG. 6B

Dataset
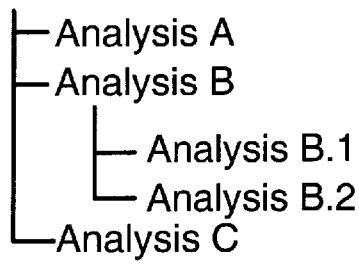
├─ Analysis A
├─ Analysis B
│   ├─ Analysis B.1
│   └─ Analysis B.2
└─ Analysis C

FIG. 6C

| Node | Parent | Child | Sibling |
|---|---|---|---|
| Dataset | nil | Analysis A | nil |
| Analysis A | Dataset | nil | Analysis B |
| Analysis B | Dataset | Analysis B.1 | Analysis C |
| Analysis C | Dataset | nil | nil |
| Analysis B.1 | Analysis B | nil | Analysis B.2 |
| Analysis B.2 | Analysis B | nil | nil |

FIG. 6D

METHODS FOR ANALYSIS OF LARGE SETS OF MULTIPARAMETER DATA

ACKNOWLEDGMENTS OF GOVERNMENT RIGHTS

This invention was made with Government support under contract no. CA42509 awarded by the National Institutes of Health. The Government has certain rights in this invention.

FIELD OF THE INVENTION

This invention relates to methods for the application of multiple discrete analyses to one or more data sets, and to methods for representing such multiple discrete analyses. More particularly, the invention relates to the use of such methods in fields such as flow cytometry, wherein multiparameter data is recorded for cells analyzed by the instrument, and the evaluation of demographic data, or the analysis and evaluation of any other complex data sets that require multiple discrete operations to be performed in succession.

BACKGROUND OF THE INVENTION

Analysis of complex data often follows a reductionist approach. In other words, discrete analysis steps are performed on the data that, in general, simplify or reduce the number of data values or group the data values into similar clusters. Further analysis steps are then carried out independently on the results of these initial algorithms until the data is finally reduced to one or more outputs that the user desires. These outputs can be as simple as a single number (for example, a mean of values), or as complex as a series of graphs representing different aspects of the data.

Visualizations of the outputs of algorithms can be as simple as a display of a single number, or as complex as a dynamic multidimensional series of graphs. The generation of a visualization is itself an algorithmic process, and is as important to the analysis of data as the functional manipulation of the data. Visualizations can be associated with any given analysis step; thus, a user can completely analyze a data sample by associating successive algorithms and viewing the associated visualization in order to monitor the analysis process.

The advantages of a reductionist approach involving discrete analysis steps is that parts of the analysis can be applied to different datasets that may require different pre-analysis For example, some datasets require smoothing or elimination of spurious data before proceeding with further analysis.

This mode of data analysis is particularly useful in the field of flow cytometry. For example, scientists studying the very heterogeneous composition of white blood cells will typically employ measurements that discriminate these cells by revealing the presence or absence of particular proteins on the cells. Some of these proteins can discriminate major classes of white blood cells (i.e., B cells vs. T cells); others can discriminate subsets of these major classes. However, most of the proteins are expressed by many of the subsets; thus, it is necessary to use a combination of many different measurements to identify unique kinds of blood cells.

Typically, a scientist will first separate flow cytometric data values into sets corresponding to the major white blood cell types. To further differentiate between subsets, the researcher will view graphs that are derived from data only corresponding to these sets. As more and more restrictions are placed on the data, finer and finer subsets of cells are identified. Once the subsets have been identified, the scientist will typically desire a variety of different statistics to be determined for the cells contained in that subset Often, the steps taken to analyze flow cytometric data can be repeatedly applied to multiple data samples. The specific gating (i.e., the restriction of the data values to particular sets) can be applied to, for example, different samples obtained from different individuals. A particular gating can also be used within the same sample to differentiate subsets of different major classes (for example, the same gating may identify subsets of B cells or subsets of T cells, depending on which data values are inputted to the algorithm). This is an underlying principle of batch analysis: the repetitive application of a series of algorithms in order to achieve similar analysis results on multiple samples.

A significant drawback of this approach is that different samples may require slightly (or significantly) different algorithms to achieve the same principal goal. In other words, in one sample, the major cell divisions may require a different type of gating than that required in another sample. However, subsequent analyses such as further gating or statistics may be identical between the two samples. Current analysis techniques do not provide the flexibility to allow for specific modification of certain algorithms within an analysis scheme while still allowing for easy batch analysis.

It will be apparent to one knowledgeable in the field of data analysis that the analysis processes and inherent limitations described above for flow cytometric data can be equally found in other types of data analysis. These include, but are not limited to, the analysis of demographic data and the analysis of clinical data. These data types are examples of highly multiparametric datasets (wherein many measurements are made for each member of the dataset) that can require complex analysis that may take many steps.

Current implementations of data analysis programs are extremely poor in the area of batch-mode analysis (i.e., repetitive analysis of multiple sample datasets). In general, batch-mode analyses are accomplished by the identical and repeated application of an algorithm, without allowing for sample-specific modifications to such algorithms. Therefore, after application of the batch process, the user must go back and re-analyze those samples requiring different steps. This process becomes especially tedious and error-prone when the batch analysis must be repeated (for example, to change one step in the batch analysis). This puts an enormous demand on the user to remember which samples require modifications of the algorithms, and what those modifications are. Current implementations also have no "automatic" mechanisms for scheduling batch analysis. Typically, users must select a set of sample data files and issue the command to apply a given algorithm to that entire set. When a new set of data samples has been collected, the user must re-issue the batch command for every algorithm to the new data samples. Finally, most implementations of data analyses do not allow the user to associate a descriptive name with the algorithms employed. The algorithms are often cryptic and difficult to immediately understand; thus, the user often will make mistakes by not recognizing subtle modifications to algorithms. Even when implementations allow users to annotate algorithms, the annotation itself has no functionality to the implementation, which tends to dissuade users from performing the annotation.

In the end, current data analysis programs place too much of a burden on users to keep track of the precise algorithms used to analyze samples. In addition, they provide few tools to employ these algorithms repetitively, and when they do provide such tools, these tools do not allow for any flexibility in the application to datasets requiring specific modifications of those algorithms.

SUMMARY OF THE INVENTION

This invention encompasses features derived from the application of three interrelated concepts to address the needs of analysis of multiple complex multiparameter datasets. In general, analysis steps are considered to be discrete algorithms that can be applied in succession or in parallel in order to carry out operations that manipulate the data. Such operations can modify the data values, reduce or increase the number of data values, or generate summary statistics; in most cases, operations can be applied to the data that results from other operations.

The first concept, "Functional equivalence by Algorithmic Polymorphism" (FEAP), allows for the referencing of mathematical (or other) algorithms by abstract names that may or may not be unique. Thus, the user or the program can assign a specific name to an analysis step to indicate what the purpose of the step is (algorithmic polymorphism). Future dependent analyses are assigned to this step by its name rather than by virtue of the precise algorithm (functional equivalence). This allows the use of distinct mathematical algorithms for any given step in analyzing different samples to be treated similarly for subsequent analysis steps.

The major benefit of FEAP is the ability to specify batch analyses on data sets with unique properties. For example, each data set may have a different precise algorithm to select the particular data values of interest for further analysis. By giving the same name to this step for all data sets (e.g., Subset A), the user can easily tabulate a derived statistic (e.g., "calculate the median for Subset A") that is applied to all sample data sets irrespective of the specific underlying algorithm.

The second concept is the visualization of the analysis steps through the use of a hierarchy. In the current inception, the use of a genealogical metaphor is employed to distinguish between dependent analyses (analyses applied to the data resulting from other analyses, called "children") and independent analyses (different analyses applied to the same data values, called "siblings"). The final result of a complex series of analysis steps is fully described by the "ancestral lineage"; in most cases, the program actually computes the output of the final data step by computing each analysis step in the hierarchy in order of descendancy. In the genealogical metaphor, the name of each analysis step must be unique among siblings, as the name is necessary for the application of FEAP. In the genealogical metaphor, the full name of any analysis step is actually a concatenation of the names of all of its ancestors; therefore, the specific name of analyses can be the same in different generations or among "cousins", since their full names will be necessarily distinct.

In batch analysis, entire "families" of analyses can be copied between different data sets, and even applied to other analysis steps. This process significantly simplifies the user interface necessary for organizing and applying complex series of analysis steps to one or more data sets.

The third concept is the use of special groups of samples to aid in the batch analysis of those samples. These special groups are named "Multi-sample surrogate groups", or MSAS. An MSAS has two kinds of members: sample data sets, and analysis hierarchies (series of analyses). An MSAS acts as a surrogate for every sample in its membership; in other words, every analysis that is applied to an MSAS is automatically applied to every sample in the MSAS.

This form of batch analysis is particularly powerful, in that it implements rigor (the same analysis process is applied to every sample) but simultaneously allows flexibility (the precise algorithms used for any given sample can be modified to be unique to that sample). Visualization cues let the user know which analyses applied to a sample are derived from an MSAS to which the sample data set belongs, which analyses are derived from the MSAS but have been modified for the specific sample data set, and which analyses are unique to the sample data set.

In one aspect of the invention a method is provided for the application of data analysis performed in multiple discrete steps, wherein the algorithm of each step can be specified without knowledge of the algorithms of preceding steps. The method is characterized by the following features:

(a) the association between an algorithm and a name ("Functional Equivalence by Algorithmic Polymorphism", or FEAP);

(b) the use of the name to denote application of the associated algorithm without regard to the specific algorithm;

(c) that algorithms associated with the same name are to be handled identically in subsequent analyses even if they are different.

In a preferred embodiment, each step is given a name that may or may not be unique, but usually connotes the general aim of the analysis step. In addition, any step may be a specification of a subset of data points on which further analysis steps are to be performed Any step may represent a mathematical computation on the data, resulting in one or more derived data values. The data may be comprised of any combination of discrete, continuous, or categorical values. For example, in one embodiment, the data relates to cells analyzed by a flow cytometer, in which one or more distinct measurements are recorded for each cell. In this embodiment, the analysis of flow cytometric sample data sample includes classifying subpopulations of cells by application of successive subsetting steps. The analysis also includes determining statistical results on specific subsets of blood cells.

In another aspect of the present invention a method is provided for the representation of multiple discrete steps of analysis of data wherein the dependence of each step on previous steps and on the specific data set being analyzed is displayed graphically. The dependent steps are represented in a hierarchical tree, where the top level of the tree represents the original data set. In addition, the analysis hierarchy is displayed using a genealogical metaphor, in which (a) dependent steps are represented as "children";

(b) independent parallel steps are represented as "siblings";

(c) the original data set is represented as the "eldest ancestor"; and (d) no two "siblings" may have the same name assigned.

The method also provides a tool for copying analysis steps between different data sets. In a preferred embodiment, this tool includes a "drag-and-drop" operation, in which (a) the user selects one or more analysis steps;

(b) the user drags the selection to a destination data set; and (c) the analysis steps are reproduced and applied to the destination data set.

The tool may also include a "copy and paste" operation, in which (a) the user selects one or more analysis steps;

(b) the user specifies that the analysis steps are to be copied, usually by a specific keystroke or menu selection;

(c) the user selects one or more destination data sets;

(d) the user specifies that the analysis steps are to be created, usually by a specific keystroke or menu selection.

In the use of the tool, the destination of the copy operation may be itself an analysis step, such that the copied analyses are created as operations dependent on the result of the destination analysis step. If the destination of the copy operation already has an analysis of the same name, one of four operations can be employed:

(a) the original analysis is replaced by the copied analysis;

(b) the copied analysis is renamed to have a unique name and then added;

(c) the original and copied analyses are merged so as to add any elements in the copied analysis not in the original, but without modification of the original elements;

(d) no addition occurs

In another aspect of the invention a method is provided for copying analyses amongst a group of sample sets by the creation of one or more "Multiple Sample Analysis Surrogates", or MSAS, such that (a) MSAS have as members a set of samples and a set of analyses, either of which may themselves have no members (the null set);

(b) all analyses that belong to an MSAS shall be applied, if possible, to all samples that belong to the MSAS;

(c) all samples belonging to the MSAS shall have all applicable analyses belonging to the MSAS;

(d) any data set can be a member of one or more MSAS; and (e) any analysis or series of analyses can be a member of one or more MSAS.

In a preferred embodiment of this method, the addition of a new sample data set to the MSAS automatically applies all analyses belonging to the MSAS to the new sample. The analyses applied to sample data sets by virtue of membership within an MSAS are visually distinguishable from analyses applied only to individual samples. Normally, analyses applied to a sample data set by virtue of membership within an MSAS can be modified only for a single sample. If there is a modification of an analysis belonging to the MSAS, it is propagated to all sample data sets belonging to the MSAS. In this case, modifications to individual samples can be disallowed through user specification or through the existence of previous sample-specific modifications of the analyses. The destination data set of an analysis copy operation may be one or more MSAS, or an analysis step belonging to one or more MSAS. One or more MSAS can be members of another MSAS, such that all analyses belonging to the "parent" MSAS are automatically members of the dependent MSAS, but all MSAS may have distinct sample dataset memberships. In addition, one or more MSAS can be members of another MSAS, such that all samples belonging to the "parent" MSAS are automatically members of the dependent MSAS, but all MSAS may have distinct analysis trees.

In another aspect of the invention a method is provided for generating tabulated data reports, employing the concept of MSAS described above, in which (a) each row in the table is created for each unique data set within the MSAS;

(b) each column in the table is created for each unique analysis type desired;

(c) each cell in the table has the result of the analysis specified by the column as applied to the sample corresponding to that row; and (d) a report is generated in which the table is printed on one or more pages or electronic documents.

In another aspect of the present invention a method is provided for generating graphical reports, employing the concept of MSAS described above, in which (a) any graphical element is a representation of an analysis step;

(b) one or more graphical elements can be a part of the report;

(c) graphical elements from each unique sample within the MSAS are collected as specified by (a);

(d) a report is generated in which each collection in (c) is placed onto one or more printed pages or electronic documents.

BRIEF DESCRIPTION OF THE DRAWINGS

FIG. 5 illustrates how the invention can be particularly useful in the analysis of highly complex data sets, such as Flow Cytometry data.

FIG. 6 defines aspects of analysis nodes (i.e., discrete analysis steps) used in the example flow charts of FIGS. 7–9.

DESCRIPTION OF THE SPECIFIC EMBODIMENTS

Figure 1A:
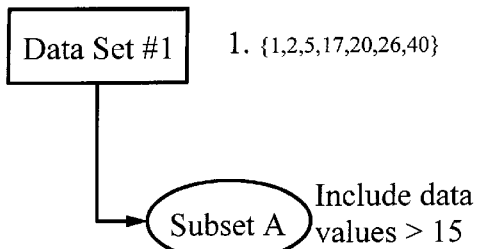
FIG. 1 illustrates a simplistic example of the concept of FEAP.
Figure 1B:
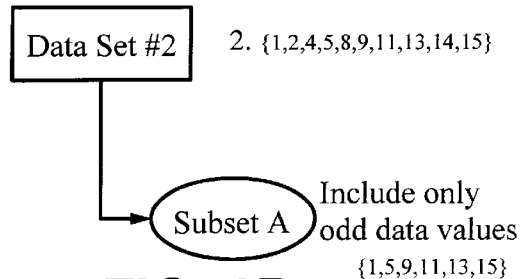

While this invention is satisfied by embodiments in many different forms, a specific embodiment created for the analysis of flow cytometry data is described in detail herein and shown in many of the FIGURES. It is understood, however, that the present disclosure is considered an example of the invention and is not intended to limit the scope of the invention to the embodiments described.

Analysis of complex multiparameter data sets often requires the successive application of many distinct algorithms that manipulate data. Multiparameter data is a collection of values where each event in the data has associated with it a set of one or more measured values. These algorithms can include operations to subset the data (select a portion of the data for further analysis), convolute the data (modify the actual data values or create additional new parameters for each event), or reduce the data by calculation of summary statistics such as means or histograms.

In many cases, each individual algorithm can be specified without knowledge of the previous steps of the analysis. For example, "Calculate Mean" specifies that the data should be reduced to a single value, the average of the data values; this operation can be specified without knowing how the data from the original data set had been manipulated.

An important concept in complex analyses of many similar data sets is that it may be necessary to have different algorithms to achieve the same end-result. For example, the user may desire to describe a central tendency of one data set using a mean; for another set, the user may wish to use the median. In either case, however, the user will wish to use the calculated value in the same way for further analyses.

In this invention, this technique is accomplished through the use of "Functional Equivalence by Algorithmic Polymorphism" (FEAP). FEAP allows the user to associate a name with an algorithm; the same name may be associated with different algorithms for different data sets (algorithmic polymorphism). Continuing in the example above, the user can name the operation to estimate the central tendency Central. For the first data set, the user specifies that Central should compute the mean; for the second data set, Central will compute the median. The user can then refer to both of these values simply by asking for the output of Central to be used in further analyses (functional equivalence). In this way, the algorithm is abstracted from the actual process; i.e., the mathematical computation (mean or median) is abstracted from what the user wishes to derive (the central tendency).

FIG. 1 shows a more detailed example of FEAP. For this example, consider the two datasets 1 and 2 (of FIG. 1A and 1B, respectively). These datasets are to be analyzed by the application of a series of methods. The methods are given names to identify them (inside the ellipses); the algorithm for each method is given in italic text next to the ellipse. The datasets themselves represent a level in the analysis hierarchy. Higher levels than the datasets could be considered to consist of experiments (in which a single experiment could contain several distinct datasets), or a database of datasets. The examples given in this disclosure should not be construed as to imply a limitation upon the utility of the concepts of hierarchical analysis to these types of examples.

The first operation in the analysis of the example of FIG. 1 is to reduce the datasets. For each example, a different algorithm is used; however, in both cases this algorithm is associated with the name Subset A. This is the basis of FEAP: the abstraction of an analysis step from the actual algorithms that might be employed. The idea is that the output of all instances of this analysis step share some common aspects that should be similarly analyzed; therefore, the user denotes this fact by naming them identically.

Figure 1C:
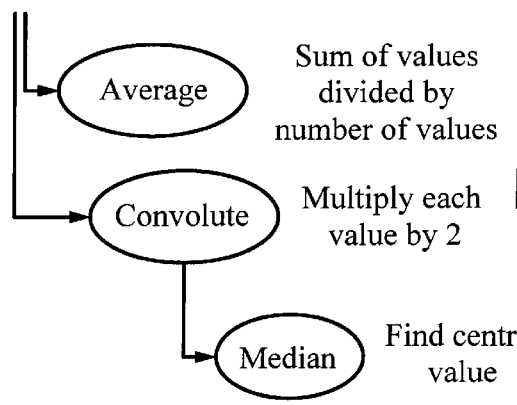
Figure 1D:
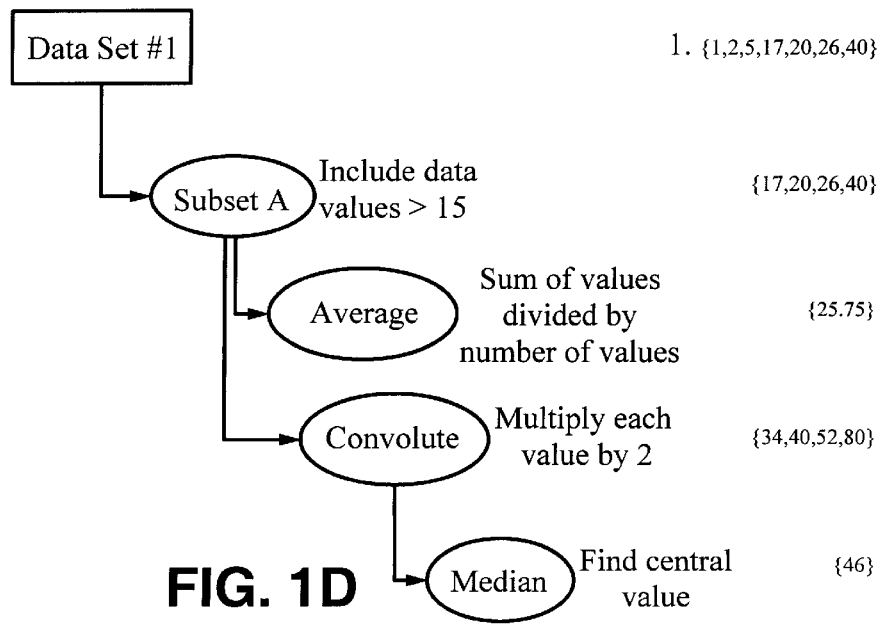
Figure 1E:
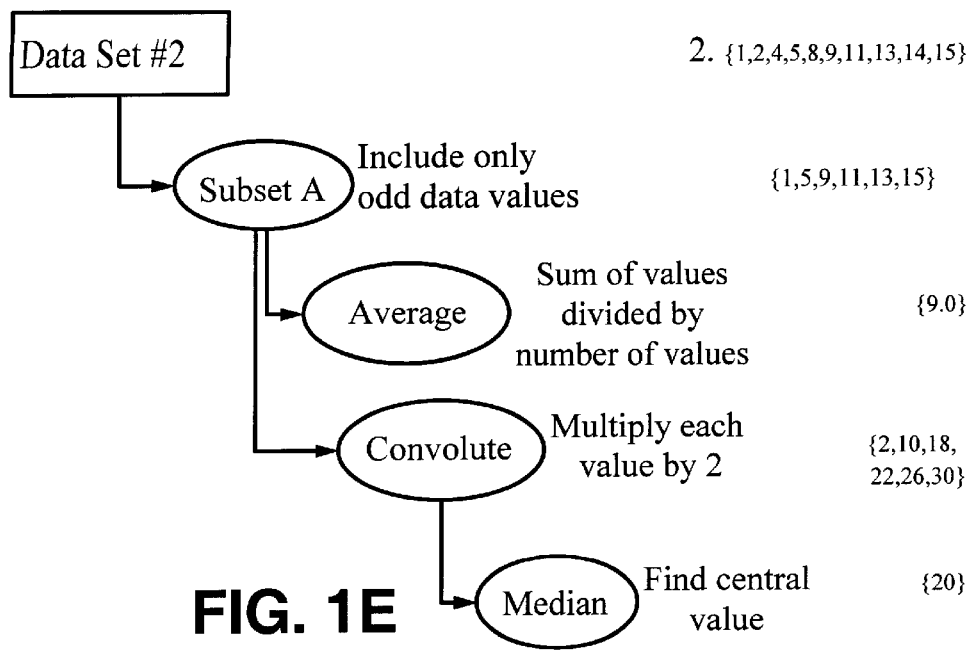

The user then wishes to apply the same series of analysis steps, as exemplified in FIG. 1C, to all datasets. In the paradigm of FEAP, the user specifies that these analysis steps should be applied to all instances of Subset A. Because of the concept of FEAP, these analysis steps are applied by the program to the output of all algorithms associated with the name Subset A irrespective of the precise algorithm employed.

Often, these different methods are domain- or case-specific. For example, consider the analysis of raw data obtained from the Hubble Telescope since its launch. Data obtained before the repair to the corrective optics required special deconvolution methods to correct for the spherical aberration in the primary reflector. Subsequent to the repair, when the correction occurs on the telescope, the data no longer requires this deconvolution, but (perhaps) a different preprocessing step. Therefore, the first data analysis step (Deconvolution) for the Hubble Telescope depends on the date of collection; subsequent analysis steps are identical and may not need to "understand" the corrections applied in the preprocessing steps.

In this manner, it will be clear that repetitive analyses can be quickly specified even when different algorithms are needed to accomplish the end result.

FIG. 1 also illustrates the use of a genealogical metaphor to visualize discrete analysis steps. In this FIGURE, the steps named Average and Convolute may be considered "siblings," as they are derivations of the same set of data values (Subset A); they are similarly considered to be "children" of Subset A. The batch analysis operations shown in FIG. 1D and FIG. 1E can be considered to be a grafting of the analysis "family" specified in FIG. 1C onto the Subset A entities.

It will be apparent that the definition of an analysis step is quite broad; it can be considered to be any combination of one or more operations, either mathematically based or not, that take as an input the result of a previous analysis step and generate an output that can be visualized or analyzed by a different analysis step.

FIG. 2 illustrates an embodiment of this invention for the analysis of flow cytometric data. Typical flow cytometric datasets contain one to twelve or more distinct measurements for each many thousands of cells. In the example of FIGS. 2–4, each dataset contains 10,000 cells for which 5 different parameters were analyzed. Furthermore, there are 4 datasets, comprising a similar staining performed on the blood cells from four different individuals. Typically, the user wishes to perform very similar operations on these datasets; most operations are called "gatings" and are data reduction operations (i.e., a gate specifies which cells are to be further analyzed). Most gates are one- or two-dimensional bounds placed on one or two parameters of the original dataset.

FIG. 2 illustrates an embodiment of this invention for the analysis of flow cytometric data. Typical flow cytometric datasets contain one to twelve or more distinct measurements for each many thousands of cells. In the example of FIGS. 2–4, each dataset contains 10,000 cells for which 5 different parameters were measured: two parameters of scattered light ("ForSc" and "OrthSc"), relating to the size of the cell, and one parameter for each of the antigens being detected (CD3, CD4, and CD8). Typical analysis of such data includes the initial divisions of the cells into clusters of major subsets based on 1 or 2 measured parameters; each of these is then divided on the basis of other measured parameters into sub-subsets. Finally, statistics may be computed on measured parameters corresponding to a defined subset of cells.

In this example there are 4 datasets, comprising a similar staining performed on the blood cells from four different individuals. Typically, the user wishes to perform very similar operations on these datasets; most operations are called "gatings" and are data reduction operations (i.e., a gate specifies which cells are to be further analyzed). Most gates are one- or two-dimensional bounds placed on one or two parameters of the original dataset.

Figure 2A:
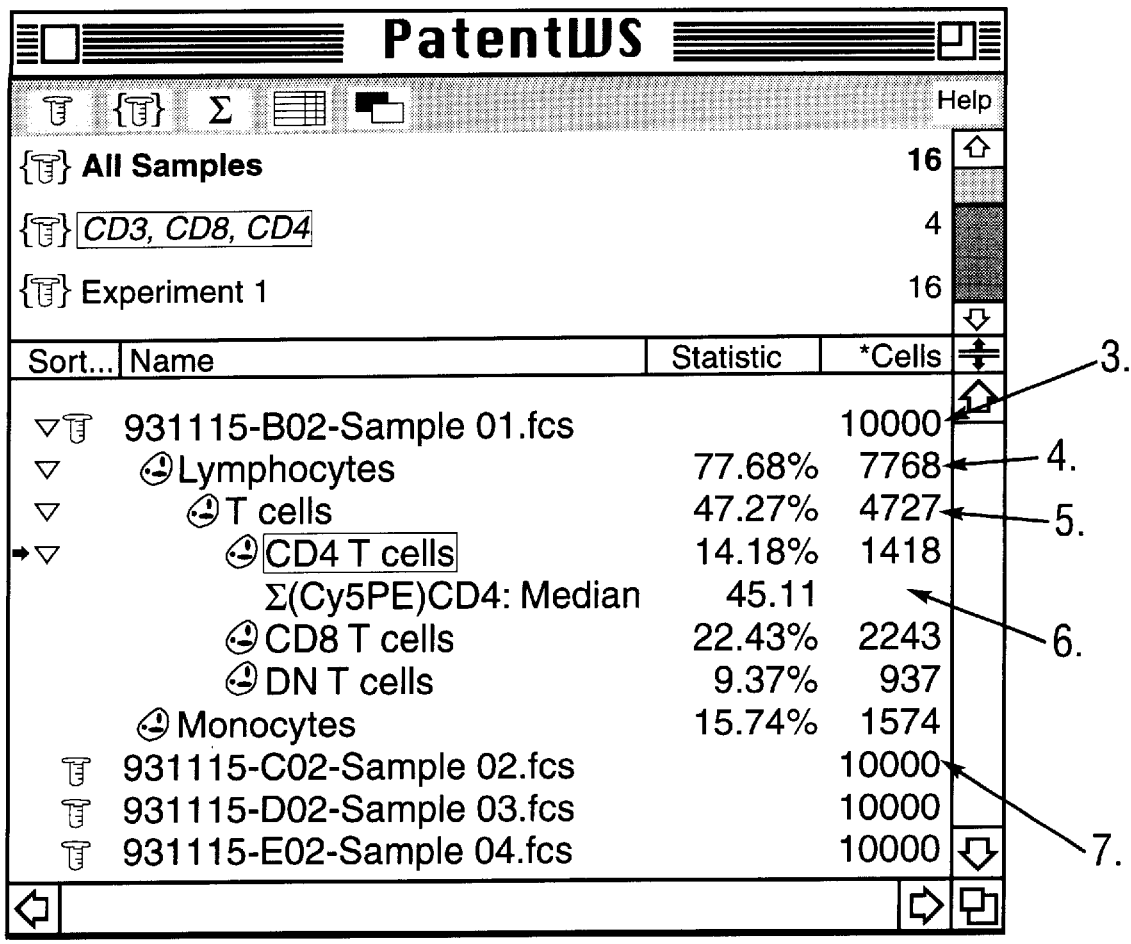
FIG. 2 illustrates an embodiment of this invention for the analysis of flow cytometric data.

In this embodiment, the sample datasets and analyses are presented to the user in the form of a "Workspace" as shown in FIG. 2A. In the lower portion of the workspace is a list of the samples (the first sample data set is 3, and then second is 7) and the analyses. Each dependent analysis is indented one additional level. In the genealogical metaphor, "T cells" (5) is a "child" of "Lymphocytes" (4); the algorithm that defines the "T cells" computation relies on its input the data from the "Lymphocytes" algorithm. Both of these algorithms are a "gating", which is a restriction of the total cell population based on one or more measured parameters. A statistic (6), the median of the Cy5PE parameter, is calculated only for cells considered to be "CD4 T cells", which must also be "Lymphocytes" and "T cells" as defined by the hierarchy.

Figure 2B:
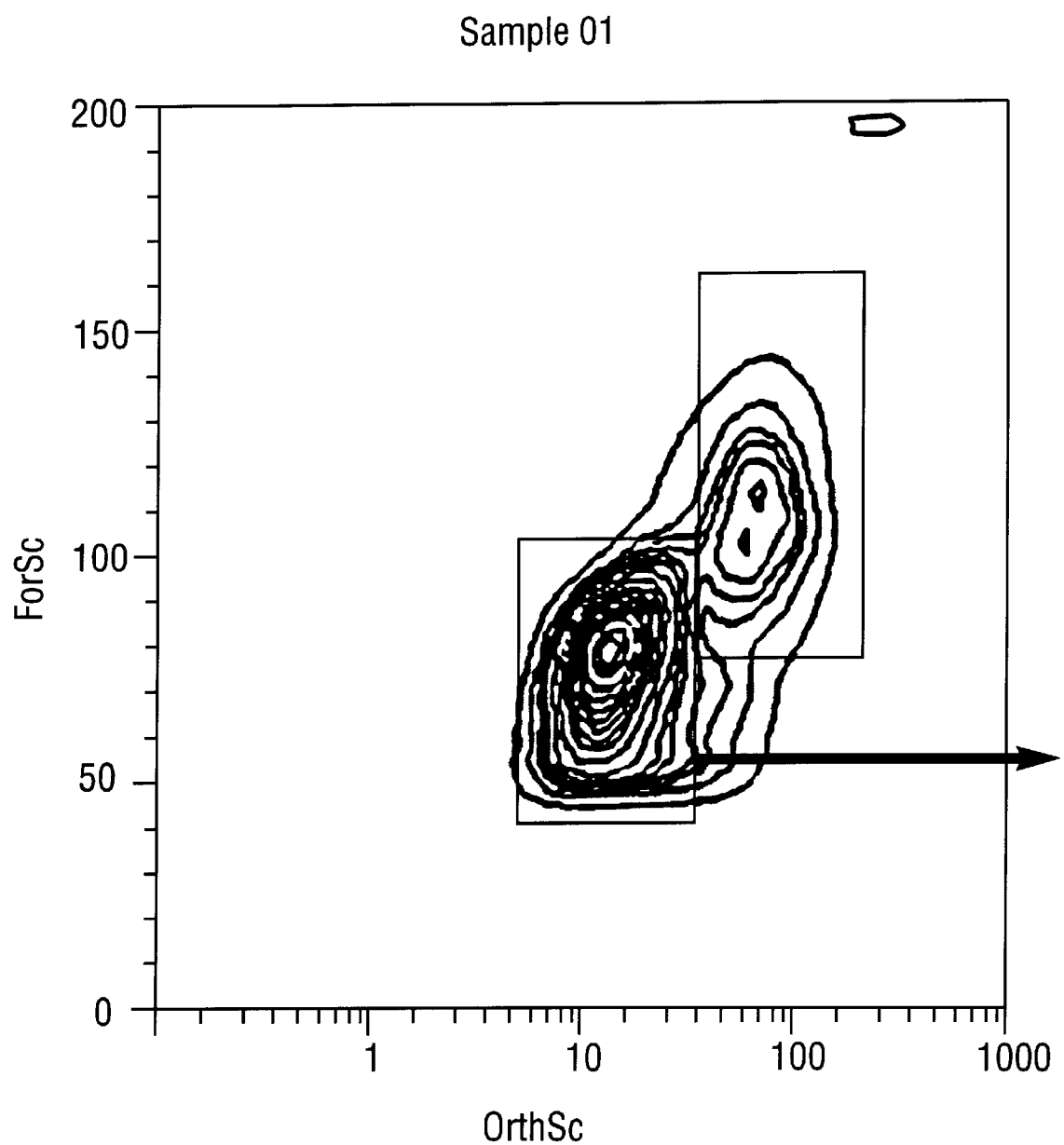
Figure 2C:
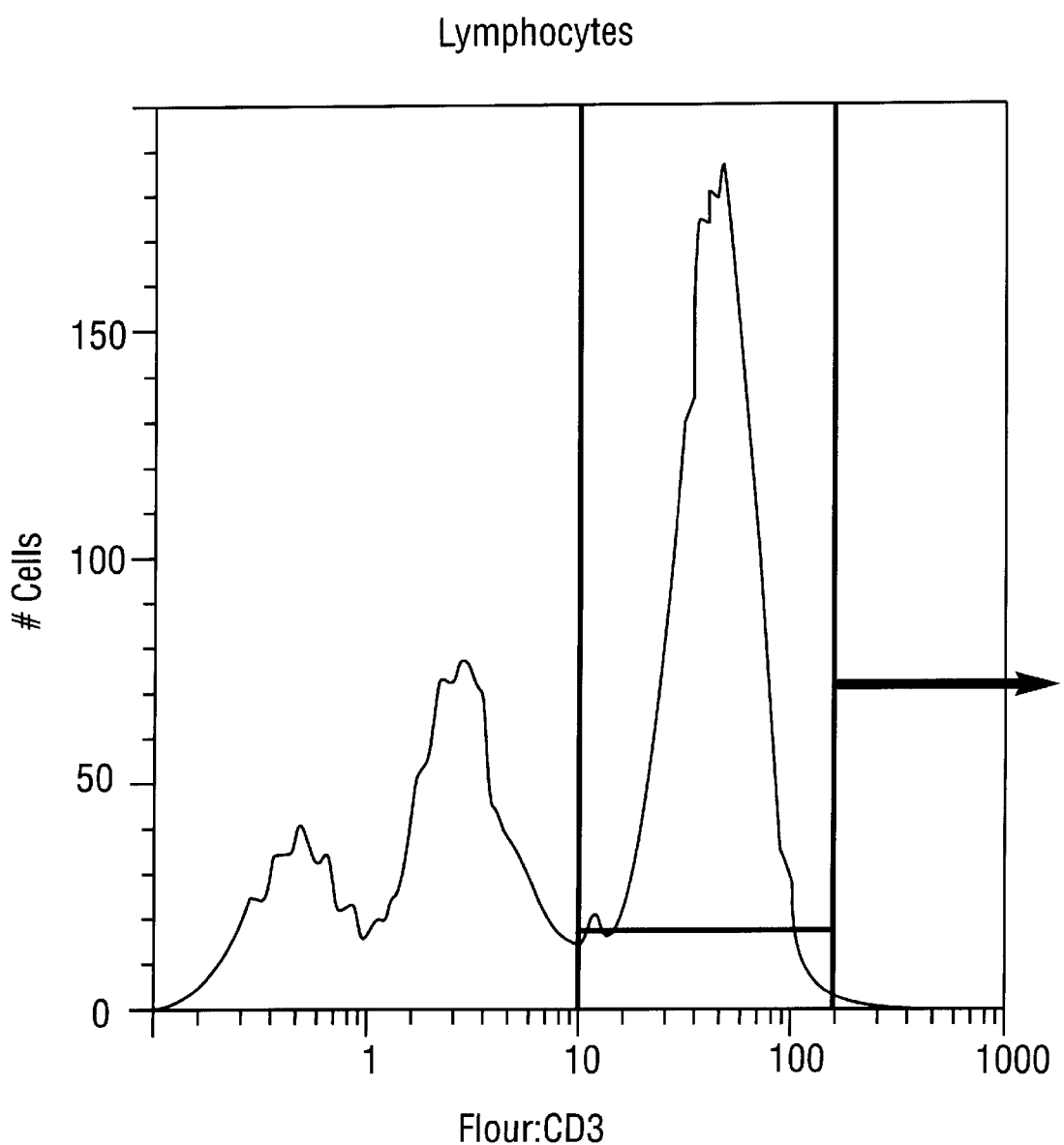
Figure 2D:
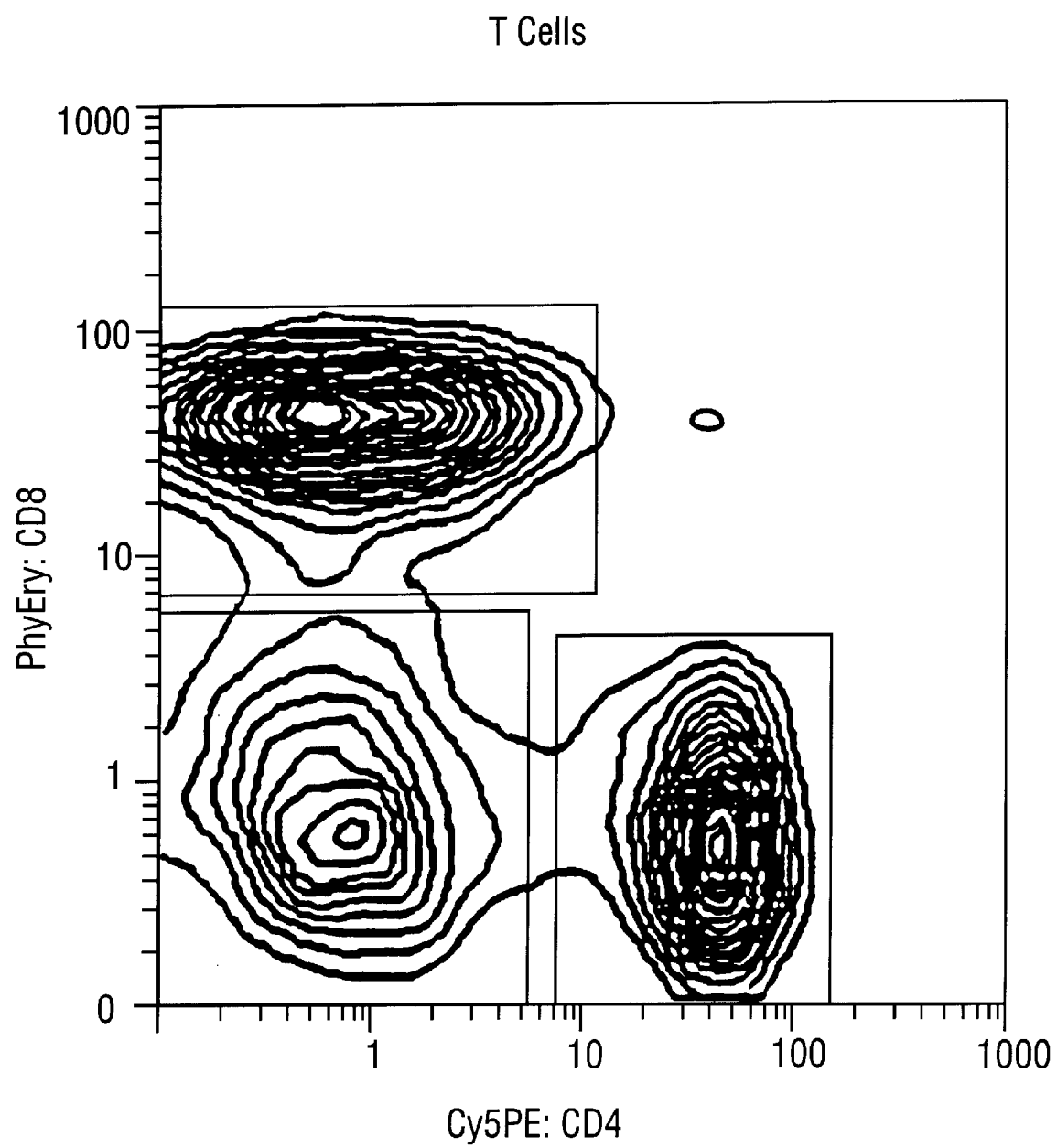

FIGS. 2B, 2C, and 2D illustrate this gating process to analyzing a blood cell sample for the representation of T cell subsets. This blood sample was stained with reagents that specifically distinguish such subsets of cells. The operation of FIG. 2B is to restrict the data to only "Lymphocytes" or "Monocytes," two of the major subsets of blood that can be distinguished by scattered light. Since T cells are only contained within Lymphocytes, the user only wishes to display the reagent measurements for the Lymphocyte cell population when considering further analysis. FIG. 2C shows the measured values for the CD3 stain for only lymphocytes; those cells with the highest CD3 values are T cells and are further selected for analysis. Finally, as shown in FIG. 2D, by examination of the CD4 versus CD8 stains of cells gated both by the "Lymphocytes" gate and the "T cells" gate, three populations of T cells are identified.

This process mimics the way in which biologists think about blood cell types: that lymphocytes are a subset of the blood (as are monocytes); T cells are a subset of lymphocytes; and CD4, CD8, and DN T cells are subsets of T cells. Note that the application of the "T cells" gate probably has no meaning for the monocytes subset; it is therefore only meaningful in the context of a "lymphocytes" gate. This hierarchy is visually displayed to a user as shown in FIG. 2A, using a genealogical metaphor similar to that in FIG. 1. In this case, each gating operation is named according the biological cell type that is identified; thus, the analysis step "Lymphocytes" is actually a selection of those data values which fall into the two-dimensional boundary drawn in FIG. 2B.

Figure 3A:
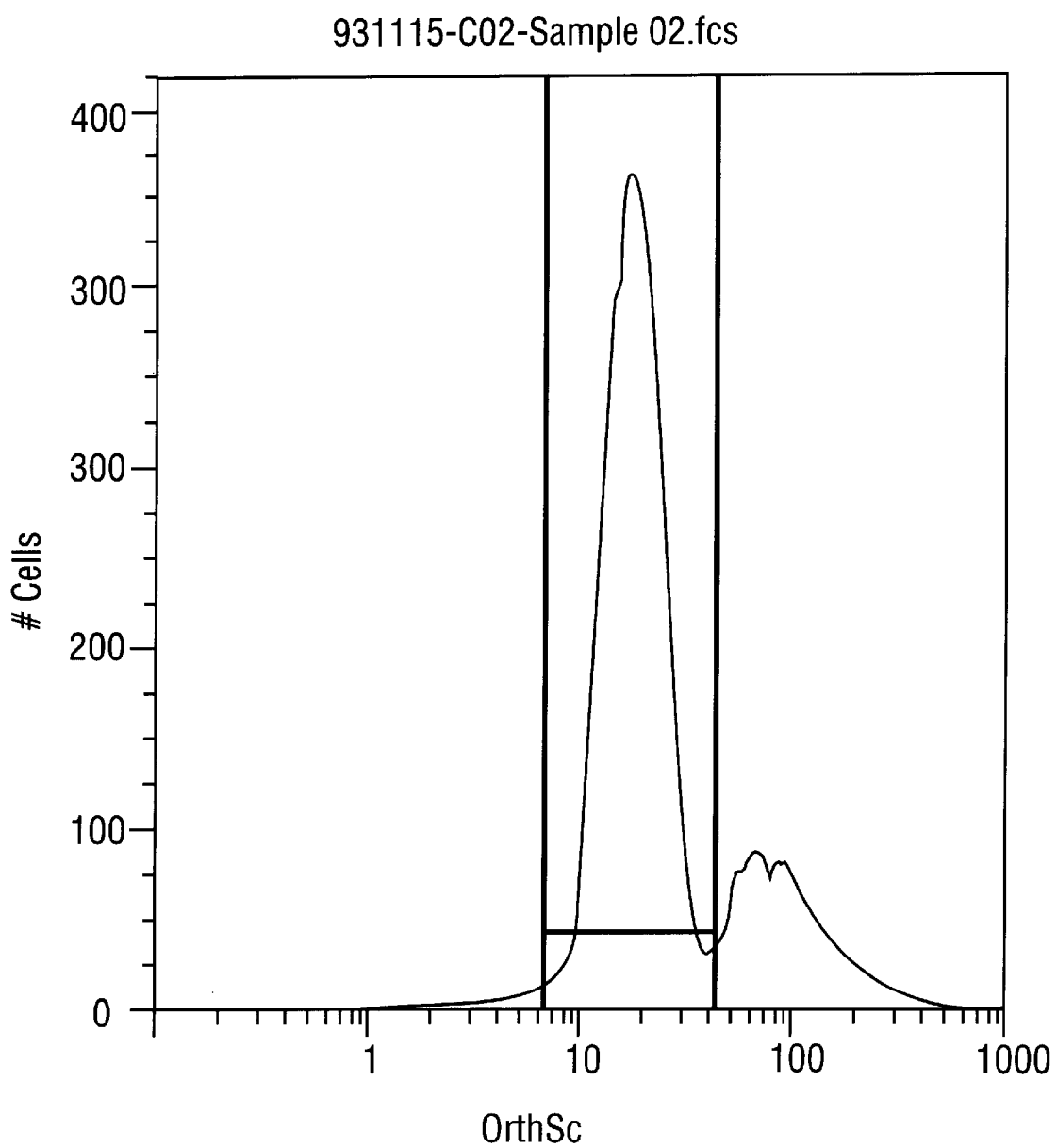
FIG. 3 illustrates the concept of FEAP using the embodiment shown in FIG. 2.
Figure 3B:
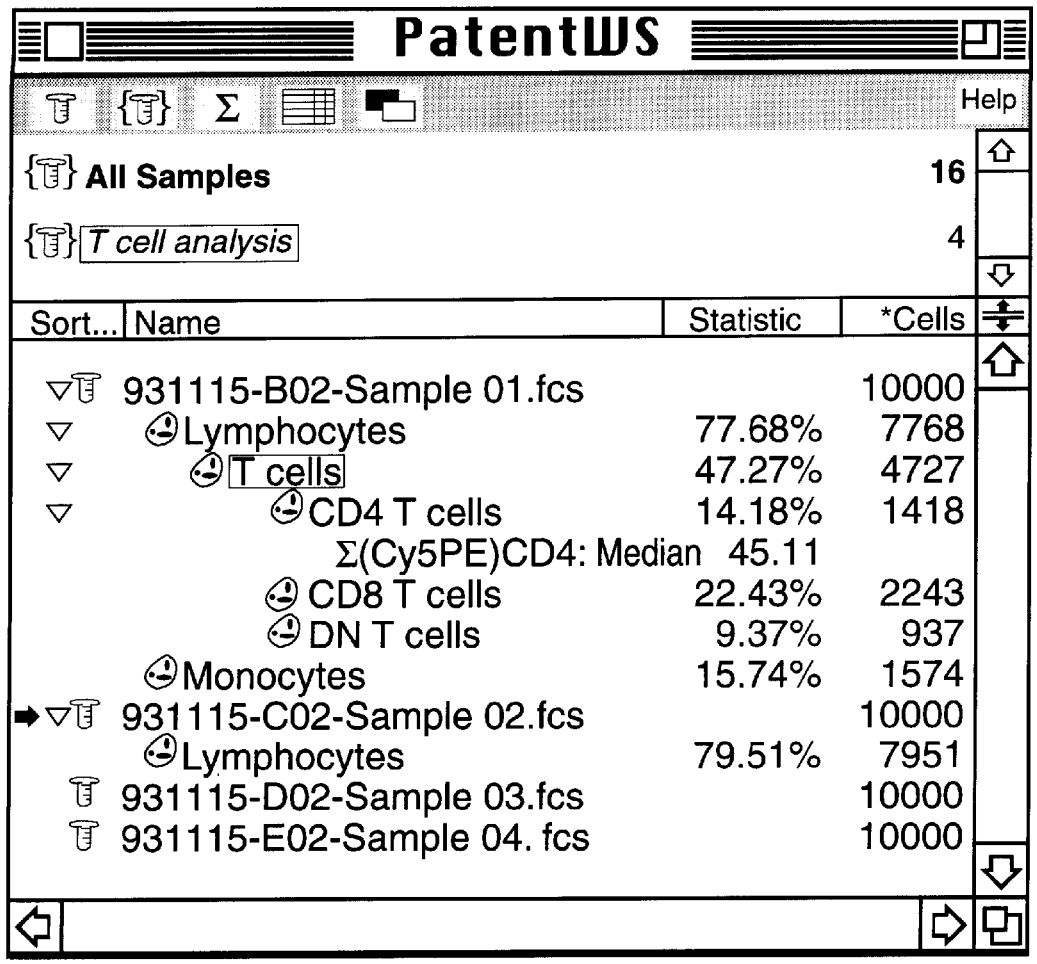

FIG. 3 continues this example for the analysis of a second dataset contained within the same experiment. However, in this case, the user wishes to use a different gate to identify Lymphocytes. As illustrated in FIG. 3A, the user specifies only a one-dimensional gate based on one of the parameters. Biologically, the meaning of these events is still "Lymphocytes", so the same name is applied as for the other sample-even though the precise algorithm deriving this subset is different. The user interface is shown in FIG. 3B, illustrating the addition of the "Lymphocyte" gating to this second sample.

Figure 3C:
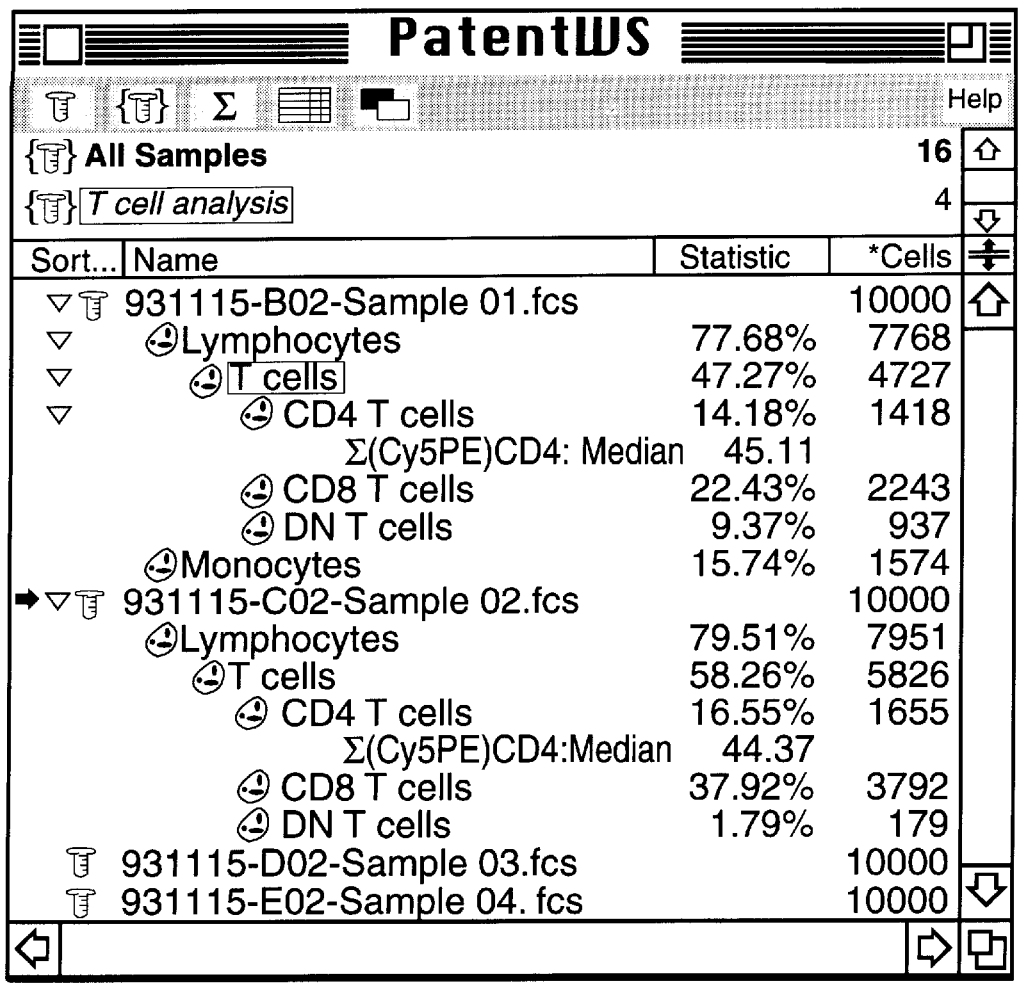
Figure 4:
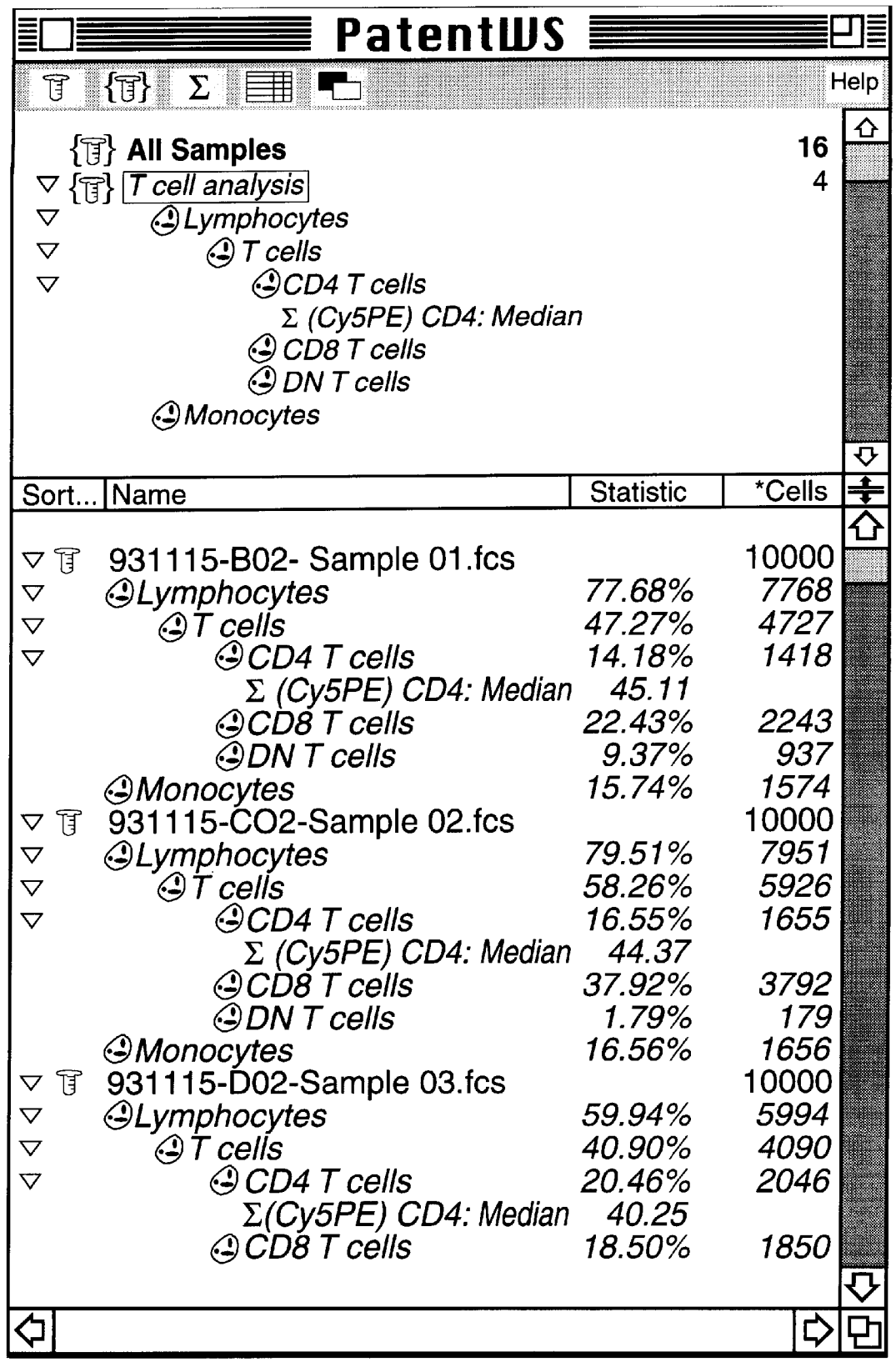
FIG. 4 illustrates the use of Multi-Sample Analysis Surrogates (MSAS) using the embodiment shown in FIGS. 2 and 3.

In FIG. 3C, the user has selected the "T cells" analysis tree (containing all of its descendants, the subsets and statistics applied to this analysis step), and copies them to the "Lymphocytes" subset of the second data set. The exact same gates, as generated on CD3 (for "T cells") or CD4 vs. CD8 (for the T cell subsets) are now mathematically applied to the data selected by the "Lymphocytes" subset. In this way, the user has quickly and easily applied an identical analysis scheme to two different analysis steps.

FIG. 4 extends these concepts by introducing the use of Multi-Sample Analysis Surrogates (MSAS). In the embodiment shown, an MSAS is created and named "T cell analysis." A MSAS is a group that contains two sets of distinct member types. The first set of members are datasets themselves; in this example, all four datasets being analyzed are specified to be members of the "T cell analysis" group. The second member type of an MSAS are analysis steps.

An MSAS is to be considered a "sample surrogate." Thus, anything that a user can do to a single sample can be done to an MSAS; the net effect is the application of that same process on every sample dataset that is a member of the MSAS, resulting in a list of outputs, each of which corresponds to a member sample of the MSAS and is identical to what would have been obtained had the analysis been applied directly to that sample.

Therefore, every analysis that is a member of the MSAS is caused to be applied to every sample belonging to that MSAS (if possible). Furthermore, should a sample be added to an MSAS at a later time, all current analyses belonging to the MSAS are immediately added to that sample. In the example of FIG. 4, the analysis family tree constructed in FIG. 2 is applied to the MSAS. This analysis is propagated to all sample data sets.

It will be apparent that the power of MSAS is beyond the batch analysis utility afforded by the properties of an MSAS. In particular, the use of an MSAS introduces "rigor" to multi-sample analysis: i.e., that every sample within an MSAS is analyzed identically The same algorithms are applied, the same order of analysis steps are applied, and every sample is fully analyzed. This function may have great importance in the analysis of data for clinical trials, wherein rigorous control of data analysis is demanded.

In the embodiment shown, however, there is a further extension of this power by allowing a level of flexibility. Specifically, sample-specific modifications of the precise algorithms underlying any given step are allowed. This feature may or may not be desirable in other embodiments; further mechanisms for extending this flexibility can also be easily conceived and should not be considered to be excluded by this description. In the current embodiment, the user can easily identify whether analyses algorithms are identical to the MSAS algorithm or whether they have been modified by virtue of the color and font style that is used to display them.

An important concept underlying FEAP is that there cannot be two analysis siblings of the same name. Therefore, rules must be defined in any given embodiment as to what will happen when an analysis of a given name is applied to a destination which already has a child with that name (functional name collision resolution). In one embodiment, the user is given four choices to resolve this occurrence: (1) "Cancel"; i.e., do not proceed with the attachment; (2) "Replace"; i.e., delete the existing analysis family and attach the new one; (3) "Rename"; i.e., give the new analysis family a unique name so that it can co-exist as a sibling to the existing analysis; or (4) "Merge"; i.e., add the unique elements of the new analysis tree to the existing one, without modification of the actual existing algorithms.

When the destination of the analysis is an MSAS, and there is a name conflict, the current embodiment selects the "Replace" option by default. Where the source of an analysis is an MSAS and the destination is a member dataset, the current embodiment selects the "Retain" option by default. Other embodiments may choose other default or user-selectable options.

It is apparent that MSAS can be used for other batch-oriented analyses. By virtue of the fact that they contain sets of datasets (as well as sets of analyses), the MSAS can be used to supply elements to a database, to a graphical report generator, or to a tabular report generator. Such report generators for displaying the results of the analysis to a user can be part of the analysis program, or a separate application program, or both. Because the MSAS are user-defined groups of datasets that typically share some common aspects, it will be common that batch analyses on these datasets are desired.

Note that MSAS can contain other MSAS as well. Any given embodiment may choose that member MSAS will automatically inherit the sample and/or analysis tree members of the parent MSAS.

FIG. 5 is an illustration of the power of the concepts of a genealogical metaphor combined with FEAP to analyze highly complex multidimensional data. This FIGURE shows a representation of the hierarchical analysis of a flow cytometric data file in which 12 parameters were measured for each of 50,000 cells. With this combination of 12 parameters, more than 2 dozen distinct types of blood cells could be identified. The hierarchy displays the ordered progression of analysis, as well as the biologically-meaningful subsetting of unique cell types. No other extant analysis schema has the ability to organize and represent such a complex analysis.

FIGS. 6–9 give details for how an implementation of the concepts described above can be programmed The implementation is simple enough to be written for any computerized platform, for example personal computers, handheld computers, or network computers. In addition, it is very well suited for highly specific hardware such as that created to control one or more instruments, in which such an implementation may represent the entirety or a part of the user interface to control the instrument for data collection, data analysis, or other data manipulation. The concepts shown in FIGS. 6–9 were used in the implementation that was described in FIGS. 2–5.

FIG. 6A provides some details about the basic unit of the hierarchical analysis tree, an "Analysis Node." An analysis node is the programmatic implementation of a single discrete element presented via the user interface to the user. Associated with each node is its name, references to other nodes in the hierarchical tree ("Parent", "Child", "Sibling"), a reference to the specific algorithm employed by that node, and information about the data required and generated by the specific algorithm.

Figure 7:
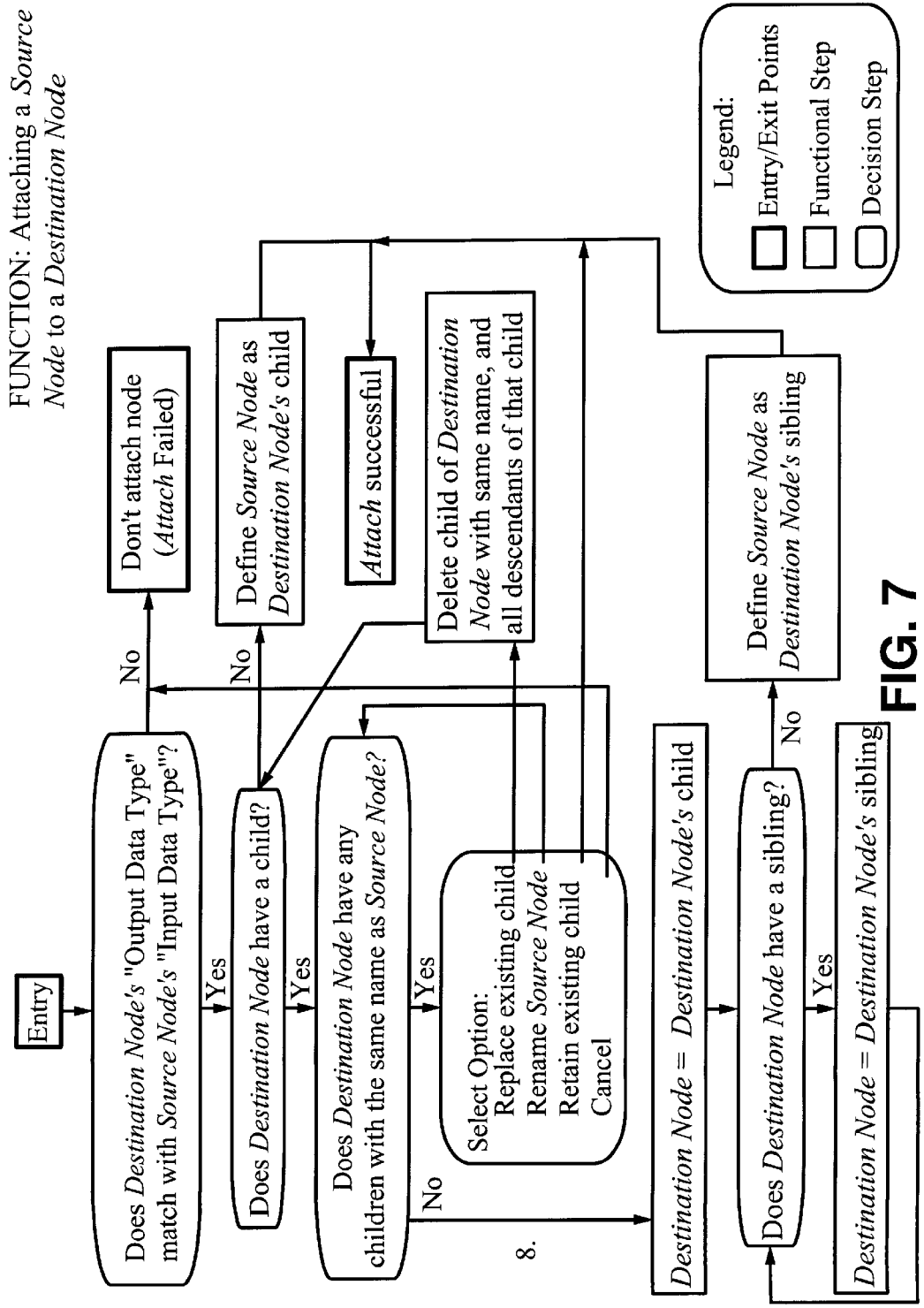
FIG. 7 is a flow chart defining how an analysis node can be copied onto another analysis node, such as shown in FIG. 1.
Figure 8:
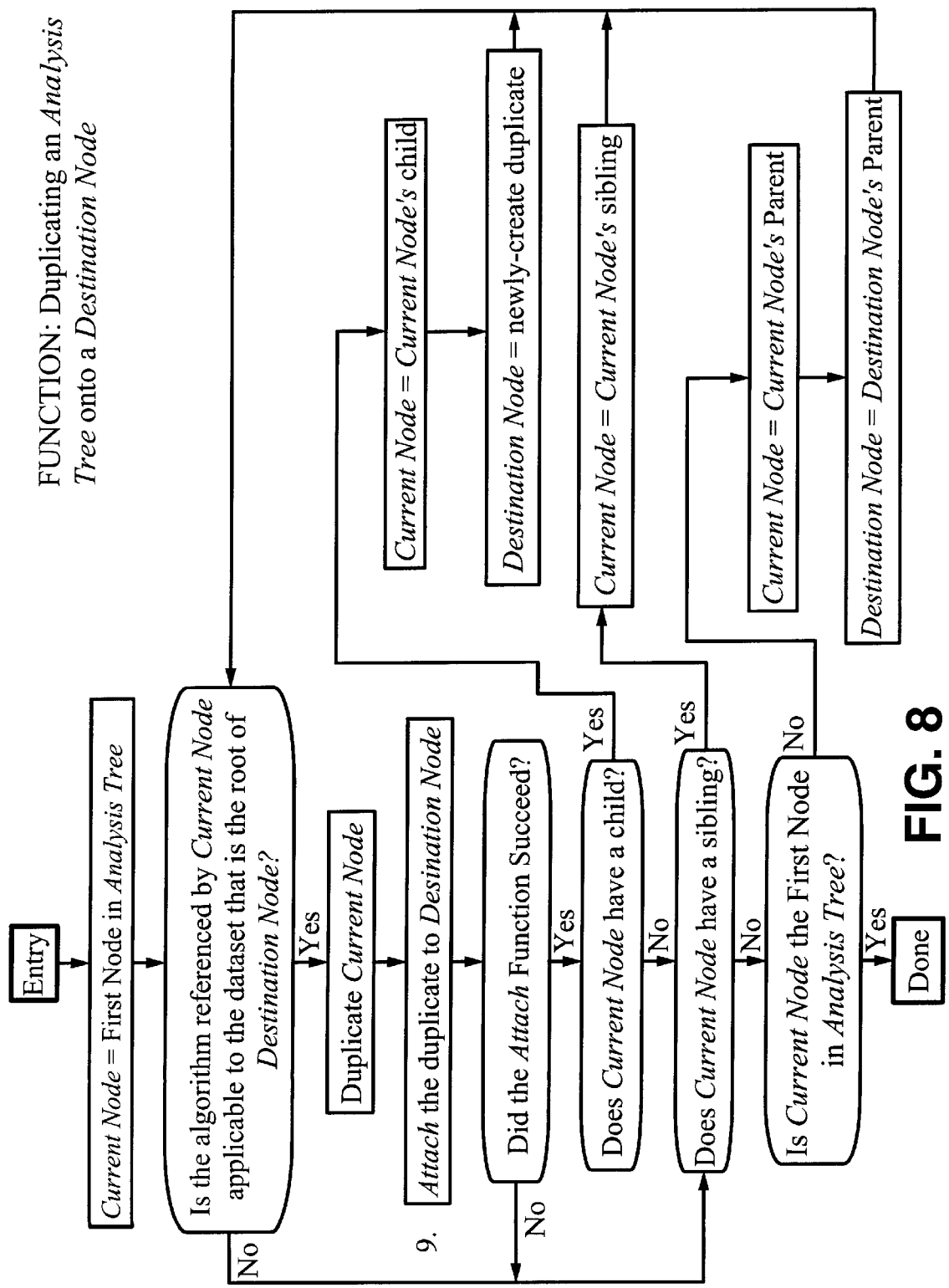
FIG. 8 is a flow chart defining how an entire set of linked analysis nodes, or an analysis tree, is copied onto a pre-existing analysis node.
Figure 9:
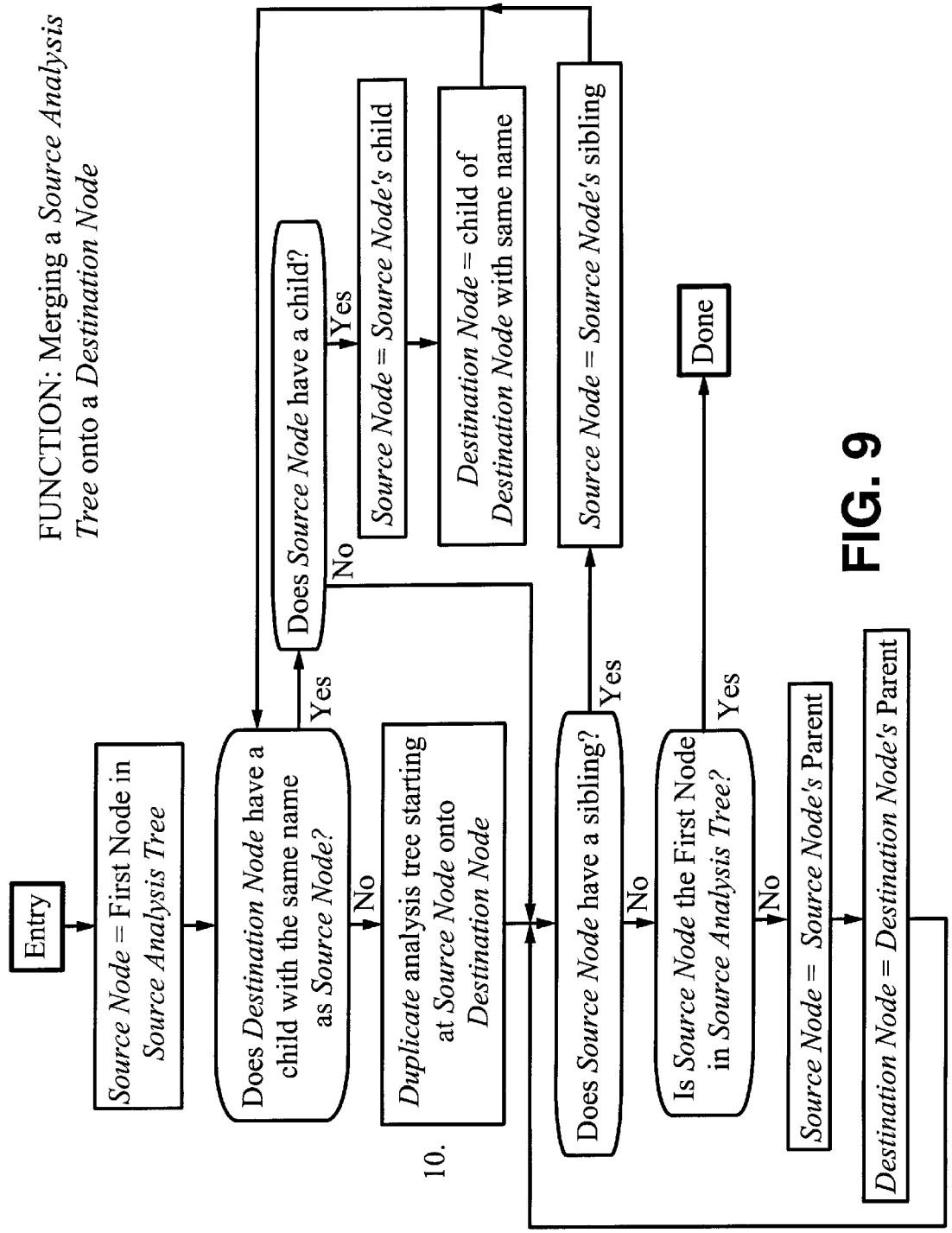
FIG. 9 is a flow chart defining how to merge two analysis trees by retaining the pre-existing analyses and only adding new nodes.

For the example Flow Charts in FIGS. 7–9, the hierarchy is defined by each node pointing solely to its parent, one of its children, and one of its siblings. The "eldest" sibling points to the next sibling, and so on; the last sibling does not point to any other siblings Only the eldest sibling is referred by the Parent as its child; other children must be accessed by stepping through the siblings one by one. There are many ways to represent a hierarchical tree; different representations would require obvious modifications of the flow charts given in FIGS. 7–9.

As FIG. 6B shows, there can be special cases of an Analysis Node, each with its own behavior For example, a sample dataset can be represented as an Analysis Node, in which the specific algorithm is a mechanism by which the data is loaded into the computer program. In this example, a sample dataset is the "root" of the analysis tree, thus having no Parent. Each sample dataset is linked to the next sample dataset by reference in the "Sibling" field.

An MSAS may itself be an Analysis Node (with the additional contents of a list of all of the sample datasets belonging to the MSAS). An MSAS has no algorithm itself, as there is no data associated with the MSAS.

FIG. 6C shows a representation of an example hierarchical analysis, consisting of three different analyses on the dataset, and two performed on the output of one of these analyses (Analysis B). The values for Parent, Child, and Sibling for each of these analysis nodes is shown in FIG. 6D in order to illustrate the representation of the hierarchical tree using this embodiment.

The computation of any given analysis node is accomplished through a simple recursive procedure. In order to generate the output from the algorithm, the analysis node must retrieve its input data from the previous step in the analysis tree (i.e., from its Parent). Thus, before computation is engaged, an Analysis Node tells its Parent to compute itself and provide the output. Because of the recursive nature of this call, no computation is performed until the root node (the dataset) is called on to compute; the root node loads the data from storage and the presents it to the child node requesting it. The recursive chain then unwinds, each analysis step computed in the correct order as specified in the analysis tree. Note that this mechanism also minimizes computational overhead, since only those analysis nodes are computed which are necessary to generate the final output (i.e., no siblings at any level are computed, since they do not affect the data passed from one node to its child).

Computation of a node is engaged by the program whenever the user requests a particular output of that node: for example, a graphical representation of the data at that stage in analysis, or the output of a statistical analysis of the data, or when the user requests a report in which an element of the report is the output of that node.

Creating these analysis trees is central to the user interface that embodies the concepts above. In general, analysis nodes are created in one of two ways: A user specifies a specific kind of analysis node should be created and attached as a child to an existing analysis node, or, the user specifies one or more existing analysis nodes should be duplicated and attached to an existing analysis node. In each case, the node to which the child analysis node is to be attached is referred to as the destination node. In each case, the program ensures that the analysis node is valid in the destination. At a minimum, this process requires that the program ensure that the type of data generated by the destination node is compatible with the type or data required by the newly-created node. In addition, the program may need to ensure that the type of analysis specified by the newly-created nodes are applicable to the dataset of which the destination node is a descendant.

FIG. 7 shows a flow chart detailing the steps necessary to attach any newly-created node (the source node) to a destination node. First, the applicability of the source node is checked; if this check passes, then the source node is made to be a child of the destination node. This process requires specifying that the source node is referenced by the Child field of destination node, unless the destination node already has a child; in that case, the source node is added as a Sibling of the "youngest" of the children of destination node.

An important feature of FIG. 7 is what happens when the source node has the same name as a child of the destination node (decision referenced 8). Because siblings with the same name are not allowed, the user must be queried as to how to resolve this problem. (Alternatively, the implementation may decide on a default decision when this process occurs. As described above, the implementation shown in FIGS. 2–6 automatically selects the "Replace" option if the destination node is a descendant of an MSAS, and automatically selects the "Retain" option if the destination node is a descendant of a dataset and the source node is a descendant of an MSAS; otherwise, the user is queried). Typically, this query is most useful when an entire analysis tree is to be copied rather than a single node. Copying entire trees is accomplished according to the steps outlined in FIGS. 8 and 9.

FIG. 8 extends the function of FIG. 7 to duplicate an entire analysis tree onto a destination node. This is the function that is called whenever the root of the analysis tree (the eldest ancestor of the tree) has a name distinct from any child of destination node. The flow chart in FIG. 7 simply iterates over all of the family members of the analysis tree, duplicating them one by one and attaching them (step referenced 9) to the appropriate place by using the function outlined in FIG. 6.

FIG. 9 extends the function of FIG. 7 to duplicate an entire analysis tree when a merging is required (i.e. when the user selects to retain existing elements that have the same name in the destination as in the source). This process makes use of the function defined in FIG. 8 (step referenced 10) to add elements whenever there is no name conflict.

The concepts described in this invention are not limited to the analysis of flow cytometric data, nor limited to the simplistic analysis algorithms given as examples This invention is generally applicable to any analysis paradigm wherein any of the following criteria exist: the need for detailed analysis of a single sample involving the application of many algorithms simultaneously or successively, analysis of multiple samples sharing some common feature, or any analyses requiring application of multiple interdependent analysis steps.

It will be apparent to one of ordinary skill in the art that many changes and modifications can be made to the invention without departing from the spirit or scope of the following claims.

What is claimed is:

1. A computer-implemented method for analyzing complex multiparameter data sets, the method comprising:

analyzing a first dataset by successive application of a first hierarchically structured set of algorithmic steps, analyzing a second dataset by successive application of a second hierarchically structured set of algorithmic steps, wherein the first and second sets of algorithmic steps are structurally and functionally equivalent, and wherein the first and second sets contain distinct but similar algorithmic steps, and displaying the analyzed data to a user.

2. The method of claim 1 wherein the distinct but similar algorithmic steps perform analogous computational functions on data sets having distinct structure but similar content.

3. The method of claim 1 wherein the first data set has a first set of parameters, the second data set has a second set of parameters, and the first set of parameters is identical to the second set of parameters.

4. The method of claim 1 wherein the first data set has a first set of parameters, the second data set has a second set of parameters, and the first set of parameters is different from the second set of parameters.

5. The method of claim 1 wherein the first data set and the second data set comprise data selected from the group consisting of discrete data, continuous data, and categorical data.

6. The method of claim 1 wherein the first data set and the second data set comprise flow cytometric data.

7. The method of claim 1 wherein the first hierarchically structured set of steps comprises top steps applied directly to the first data set, and dependent steps applied to data resulting from application of the top steps.

8. The method of claim 1 wherein the first hierarchically structured set of steps comprises analysis steps and data display steps.

9. The method of claim 8 wherein the analysis steps comprise subset selection steps and computational steps.

10. The method of claim 8 wherein the analysis steps comprise a parent step and children steps, wherein the children steps analyze data resulting from the parent step.

11. The method of claim 8 wherein the data display steps comprise generating a display chosen from the group consisting of a data graph and a data table.

12. The method of claim 1 further comprising displaying a graphical representation of the first hierarchically structured set of steps to the user.

13. The method of claim 12 wherein the graphical representation is a tree structure that displays the hierarchical dependence between the steps.

14. The method of claim 12 wherein sibling steps in the graphical representation have distinct labels.

15. The method of claim 12 wherein customized steps are displayed with a visual mark distinguishing them from uncustomized steps.

16. The method of claim 1 further comprising enabling the user to generate a duplicate of a hierarchically structured set of steps, and apply the duplicate to a specified data set.

17. The method of claim 16 wherein the user is enabled to generate the duplicate by selecting a portion of a graphical representation of the hierarchically structured set to be duplicated, and specifying a data set to which the duplicate is to be applied.

18. The method of claim 16 wherein the specified data set is a result of analysis steps.

* * * * *